(12) United States Patent
Mulder

(10) Patent No.: US 7,914,675 B2
(45) Date of Patent: Mar. 29, 2011

(54) ANAEROBIC PURIFICATION OF HEATED WASTE WATER

(75) Inventor: Albert Jacob Mulder, Tilburg (NL)

(73) Assignee: Biothane Systems International B.V., Delft (NL)

( * ) Notice: Subject to any disclaimer, the term of this patent is extended or adjusted under 35 U.S.C. 154(b) by 103 days.

(21) Appl. No.: 11/993,838

(22) PCT Filed: Jun. 26, 2006

(86) PCT No.: PCT/NL2006/000313
§ 371 (c)(1),
(2), (4) Date: Jan. 20, 2009

(87) PCT Pub. No.: WO2006/137735
PCT Pub. Date: Dec. 28, 2006

(65) Prior Publication Data
US 2009/0266761 A1    Oct. 29, 2009

(30) Foreign Application Priority Data

Jun. 24, 2005    (EP) ..................................... 05076461

(51) Int. Cl.
*C02F 11/04* (2006.01)
*C02F 3/28* (2006.01)
(52) U.S. Cl. ........................................ 210/603; 210/612
(58) Field of Classification Search .................. 210/603, 210/612, 613, 615, 631
See application file for complete search history.

(56) References Cited

U.S. PATENT DOCUMENTS

| | | | | |
|---|---|---|---|---|
| 4,632,758 A * | 12/1986 | Whittle | .......................... | 210/603 |
| 5,507,946 A * | 4/1996 | Stearns | .......................... | 210/202 |
| 6,117,672 A * | 9/2000 | Breckenridge | ............... | 435/266 |
| 6,261,447 B1 * | 7/2001 | Van Herle et al. | ............. | 210/175 |
| 2010/0206791 A1 * | 8/2010 | Lee et al. | ........................ | 210/151 |

FOREIGN PATENT DOCUMENTS

| | | |
|---|---|---|
| DE | 29 13 034 | 10/1980 |
| DE | 93 10 503 | 2/1994 |
| JP | 04-110097 | 4/1992 |
| JP | 2001107701 | 4/2001 |

OTHER PUBLICATIONS

International Search Report for PCT/NL2006/000313, mailed on Oct. 4, 2006, 3 pages.

* cited by examiner

*Primary Examiner* — Fred Prince
(74) *Attorney, Agent, or Firm* — Morrison & Foerster LLP

(57) ABSTRACT

The invention is directed to a process for the anaerobic purification of waste water in an anaerobic reactor, said process comprising burning the biogas produced in the purification, in a gas-burner, using the hot gases obtained thereby for indirect heating of water in a hot water boiler, which boiler is connected with the reactor by means of a line between the gas head of the boiler and a compartment through which the waste water flows, such as a conditioning tank or the anaerobic reactor, which line ends underneath the water level in the said compartment at such a level that a pressure of between 0.25 and 3 m of water column is maintained in the gas head of the boiler, in which boiler steam is generated which enters the said compartment through the said line and heats the waste water, and wherein the said boiler is further provided with a valve to let off steam in case the amount of biogas is in excess of the amount needed to heat the waste water.

2 Claims, 2 Drawing Sheets

ANAEROBIC PURIFICATION OF HEATED WASTE WATER

CROSS-REFERENCE TO RELATED APPLICATIONS

This application is the national phase of PCT application PCT/NL2006/000313 having an international filing date of 26 Jun. 2006, which claims priority from European Application No. 05076461.2 filed 24 Jun. 2005. The contents of the above applications are incorporated by reference herein in their entirety.

The present invention is in the area of anaerobic waste water purification and more in particular anaerobic sludge systems.

Anaerobic sludge bed reactor systems utilise anaerobic bacteria to convert pollutants in wastewater to biogas. These anaerobic bacteria grow in aggregates, often referred to as granular biomass. The systems are often characterised by low net biomass production (typically 2-3% of converted COD) as a result of the low net yield of anaerobic bacteria involved. This is a significant system advantage, as the excess biomass developed in wastewater treatment systems has to be disposed as a solid waste, at significant cost. Some of these systems are known as UASB, EGSB, IC etc, and are used commercially.

The purification process generally comprises a system, wherein fresh wastewater is introduced in the bottom of an upflow reactor, containing dispersed biomass in (partly purified) wastewater. During the anaerobic purification process, biogas is produced and a mixture of water, biomass and gas flows upward in the reactor. Before purified wastewater can be discharged, a gas-liquid-solid separation has to take place.

The biogas is often burned in a flare, as the use as fuel gas tends to be rather costly and uneconomical, due to the required investments for this.

The optimal temperature for the anaerobic purification generally is in the range of 10 to 75° C. but preferably 25 to 40° C. During cold periods this means that the waste water has to be heated. Conventionally this is done using a gas or oil fired burner or steam injection, with or without the use of heat exchangers.

From a view point of environment it would be advantageous if at least part of the energy for the heating of the waste water could be provided by the biogas. Use of biogas in a conventional burner, instead of fuel gas, still requires the treatment of the biogas. Biogas is generally saturated with water, which makes it necessary to make sure that no water condenses in the burner and further it still requires the presence of a flare to flare off the excess biogas in case no heating is required, such as during warm periods.

Various heating systems using biogas have been described. In DE-A 2913034 a regular system using a heat exchanger in the water to be heated is disclosed. In DE-U 9310503 a system has been described, wherein the hot gases from the burning of the biogas are directly introduced into the water to be heated. In the abstract of JP-A the use of biogas for heating a standard boiler is described.

Accordingly it would be advantageous if the heating of the waste water in an anaerobic waste water purification system could be performed using biogas, however, without the need for a flare and without the need for heat exchangers.

The invention is based thereon that the biogas is used in a specific way, which avoids the disadvantages of the conventional uses and makes it possible to dispense with the use of a flare.

More in particular the invention is based thereon, that biogas is used to produce low-grade steam from water, which steam is used to heat the waste water, either prior to the actual purification, i.e. during conditioning, or during the actual purification.

In a first embodiment the invention concerns a process for the anaerobic purification of waste water in an anaerobic reactor, wherein anaerobic sludge is used to purify waste water and to produce biogas, in which process the waste water is conditioned prior to the anaerobic purification in a compartment separate from the said reactor,
the biogas is burned in a gas-burner,
the hot gases obtained thereby are used for indirect heating of water in a hot water boiler, which boiler is connected with the said compartment by means of a line between the gas head of the boiler and the said compartment, which line ends underneath the water level in the said compartment at such a level that a pressure of between 0.25 and 3 m of water column is maintained in the gas head of the boiler, in which boiler steam is generated which enters the reactor through the said line and heats the waste water,
following which the waste water is introduced into the said reactor in which it is purified, and wherein the said boiler is further provided with a valve to let off steam in case the amount of biogas is in excess of the amount needed to heat the waste water.

In another embodiment the invention concerns a process for the anaerobic purification of waste water in an anaerobic reactor, wherein anaerobic sludge is used to purify waste water and to produce biogas, in which process the biogas is burned in a gas-burner, the hot gases obtained thereby are used for indirect heating of water in a hot water boiler, which boiler is connected with the reactor by means of a line between the gas head of the boiler and the reactor, which line ends underneath the water level in the reactor at such a level that a pressure of between 0.25 and 3 m of water column is maintained in the gas head of the boiler, in which boiler steam is generated which enters the reactor through the said line and heats the waste water, and wherein the said boiler is further provided with a valve to let off steam in case the amount of biogas is in excess of the amount needed to heat the waste water.

In a third embodiment the invention comprises a process for heating waste water to be treated anaerobically using biogas produced by the anaerobic purification, said process comprising burning the biogas in a gas-burner, using the hot gases obtained thereby for indirect heating of water in a hot water boiler, which boiler is connected with the reactor by means of a line between the gas head of the boiler and a compartment through which the waste water flows, which line ends underneath the water level in the said compartment at such a level that a pressure of between 0.25 and 3 m of water column is maintained in the gas head of the boiler, in which boiler steam is generated which enters the said compartment through the said line and heats the waste water, and wherein the said boiler is further provided with a valve to let off steam in case the amount of biogas is in excess of the amount needed to heat the waste water.

The process of the invention is basically based on a system, wherein the biogas is burned continuously. In case of too much biogas, heat is regulated by means of venting of excess steam. In case additional heat is required an additional burner that is fuelled with gas or liquid fuel (such as gas oil) is used. The produced heat from the burned biogas is transferred by indirect heating to water in a boiler, thereby generating steam of low temperature. This steam is directly introduced into either the anaerobic reactor, or in the conditioning compartment, underneath the water level, thereby heating the waste water. The pressure of the steam, and thus the temperature is maintained by the location where the steam is introduced in the water, i.e. the water head above the exit of the feed line for the steam. Further, the boiler is provided with a valve to let off steam in case the amount of biogas is in excess of the amount needed to heat the waste water.

This process of the invention thus provides for a very elegant and easy way to use biogas in heating the waste water. All biogas is used to fire the boiler and if more biogas is produced, the excess of heat is simply discharged via the excess steam valve in the boiler. This means that the biogas burner is not regulated by the heat requirements and a flare can be dispensed with. In fact, one could say that the biogas burner acts as flare as well. This is a substantial saving in investment and operational cost.

Further advantages of the present process are that there are no heat exchangers necessary, that are in contact with the actual waste water. The heat exchangers are in clean water, which requires substantial less maintenance.

Further, the pressure in the steam boiler is very low, namely corresponding to the head of water above the outlet of the open steam. This is much lower than the standard pressures in a low-pressure boiler, which corresponds typically to a temperature of at least 110° C., whereas in the invention it will be at most 107° C. In a preferred embodiment, the biogas is preheated (dried) by indirect heating in the boiler. This is simply done by directing the feed line of the biogas through the boiler. As biogas is saturated with water, it would normally be necessary to dry the biogas prior to burning, as conventional gas burners cannot cope with condensing gases. In the present embodiment, this can be dispensed with, as due to the heating the biogas has a temperature well above the condensation temperature thereof. This is of course a substantial saving, both in terms of investment and of operational costs.

A further saving is obtained by the absence of pumps for the heating of the waste water to be purified. Usually, this requires pumping hot water through heat exchangers. In the present case, this is not required, as the heat transfer occurs in such a way, that no pumps are required.

Important advantages of the process of the invention reside therein that a much more simple design can be applied. This means not only an important reduction in investments, but also a substantial decrease in operational costs. Also the operation is more easy and simple. This makes it possible to apply this type of purification to situations where it was previously uneconomical to do so.

As indicated above, the essential part of the invention resides therein that the biogas is burned continuously and the only that part of the heat thereof that is needed for heating the waste water is used. All the heat generated by the burning of the biogas is converted to steam. However, only the amount of steam necessary to heat the waste water to the required temperature is used, the remainder is flashed off. This means that the heating of the waste water in not regulated by the amount of gas used, but by the amount of steam introduced into the conditioning compartment. In case the amount of biogas is too low, it may be possible to use an additional burner to supply heat, for example a gas or fuel fired burner. As this burner can be operated in the same way as the biogas burner, no further additional equipment is needed, more in particular no extra boiler.

The way the various aspects of the invention may be incorporated into the anaerobic purification process is well known to the skilled person.

One of the aspects of the invention is the hot water boiler or water heating compartment. In this boiler or compartment, clean water is indirectly heated to boiling temperature, which of course depends on the pressure in the overhead compartment. This pressure is determined by the location of the end of the feed line into the compartment containing the water to be heated. This pressure corresponds in general to a water head of between 0.25 an 3 m. resulting in a water temperature of between 100 and 107° C.

The steam produced can accordingly be introduced into a conditioning tank, in which the waste water is conditioned. This includes heating the water to the correct temperature, adding any nutrients and other components necessary for the anaerobic purification, pH adjustment using acids or caustic and the like. In another embodiment the steam may be directly introduced into the anaerobic purification system.

The actual construction of the installation is not critical. The materials that are usual for the construction of anaerobic waste water purification units can be used, such as metallic and non-metallic construction materials. Also the relative placing of the various compartments can be chosen freely.

In a preferred embodiment both the compartment in which the waste water is heated by the direct steam injection and the hot water boiler are separate compartments of one housing, adjacent to each other, with an insulating wall between them.

BRIEF DESCRIPTION OF THE DRAWINGS

The invention is now elucidated on the basis of the attached figures, wherein in FIG. 1 a first embodiment is schematically disclosed, in which embodiment the direct steam injection takes place in a separate conditioning compartment, whereas in FIG. 2 a second embodiment is schematically disclosed, in which embodiment the direct steam injection takes place directly into the anaerobic reactor.

DETAILED DESCRIPTION OF THE INVENTION

Figure 1:
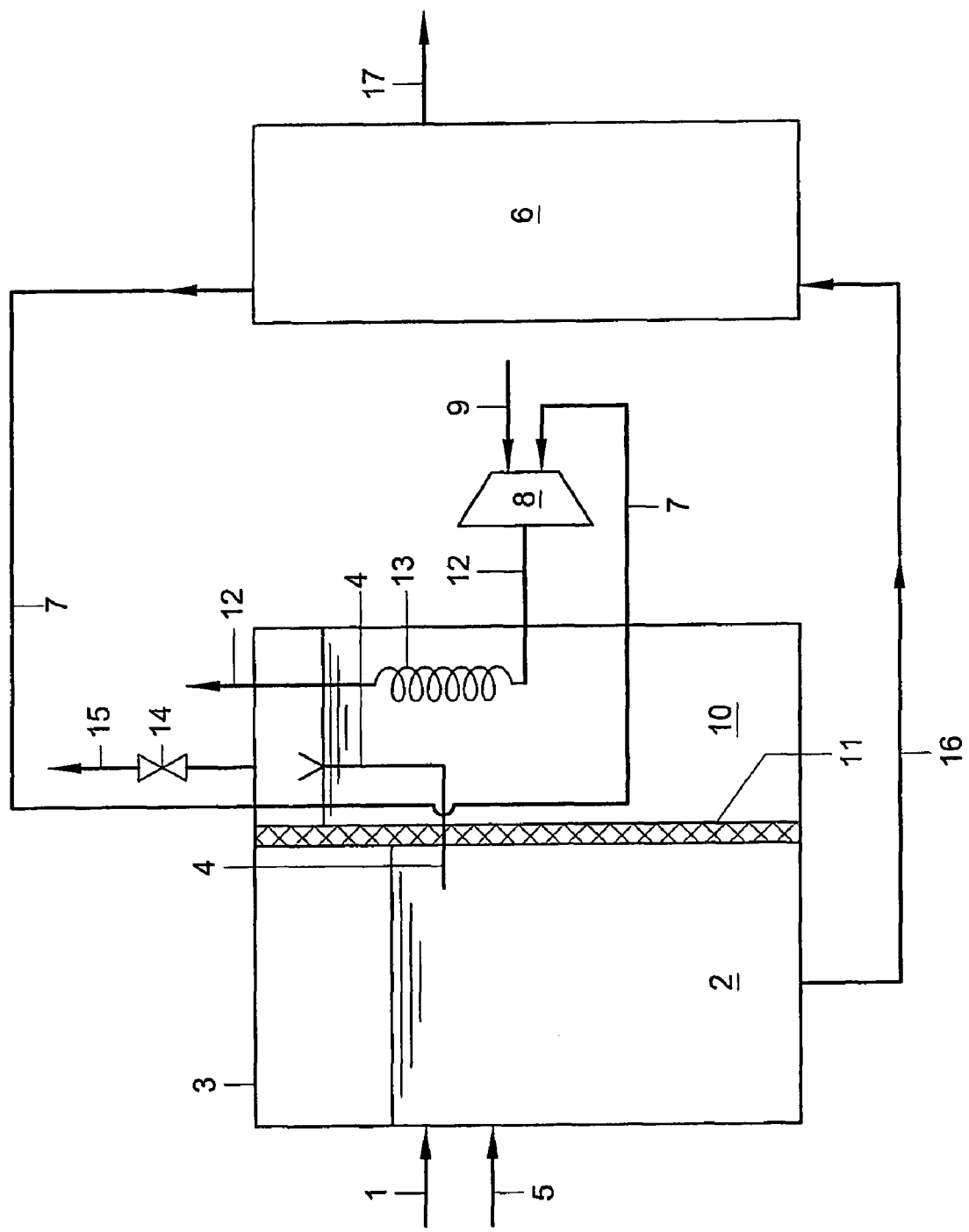

In FIG. 1 waste water is introduced through line 1 into the first section 2 of housing 3. This first section 2 is a conditioning tank or compartment, in which section 2 the waste water is brought on the required temperature (if necessary) by the injection of steam through line 4. Further nutrients may be added here through line 5, as well as pH adjusting agents (caustic and acids). Biogas produced in anaerobic reactor 6 is fed through line 7 to burner 8, together with air introduced into the burner through line 9. The biogas is heated indirectly in a second section 10 of housing 2 by passing the line 7 through the hot water in section 10. The first section 2 and the second section 10, are separated from each other by an insulating wall 11. The hot gases from burner 8 are passed through line 12 into heat exchanger 13, thereby heating the clean water in section 10. Off-gases are vented to the atmosphere. The overhead compartment of section 10 is connected through line 4 with the interior of section 2. By the pressure of the water head above the outlet of line 4 underneath the surface of the waste water in section 2, a pressure is maintained in section 10, which pressure determines the temperature of the steam generated in section 10. This steam passes through line 4 to section 2 and heats the waste water to the required temperature. In case no heat is needed to heat the waste water, or in case less heating is needed that could be generated, excess steam is vented through valve 14 and line 15 to the atmosphere The waste water is fed through line 16 to an anaerobic reactor 6 and purified effluent is collected through line 17.

Figure 2:
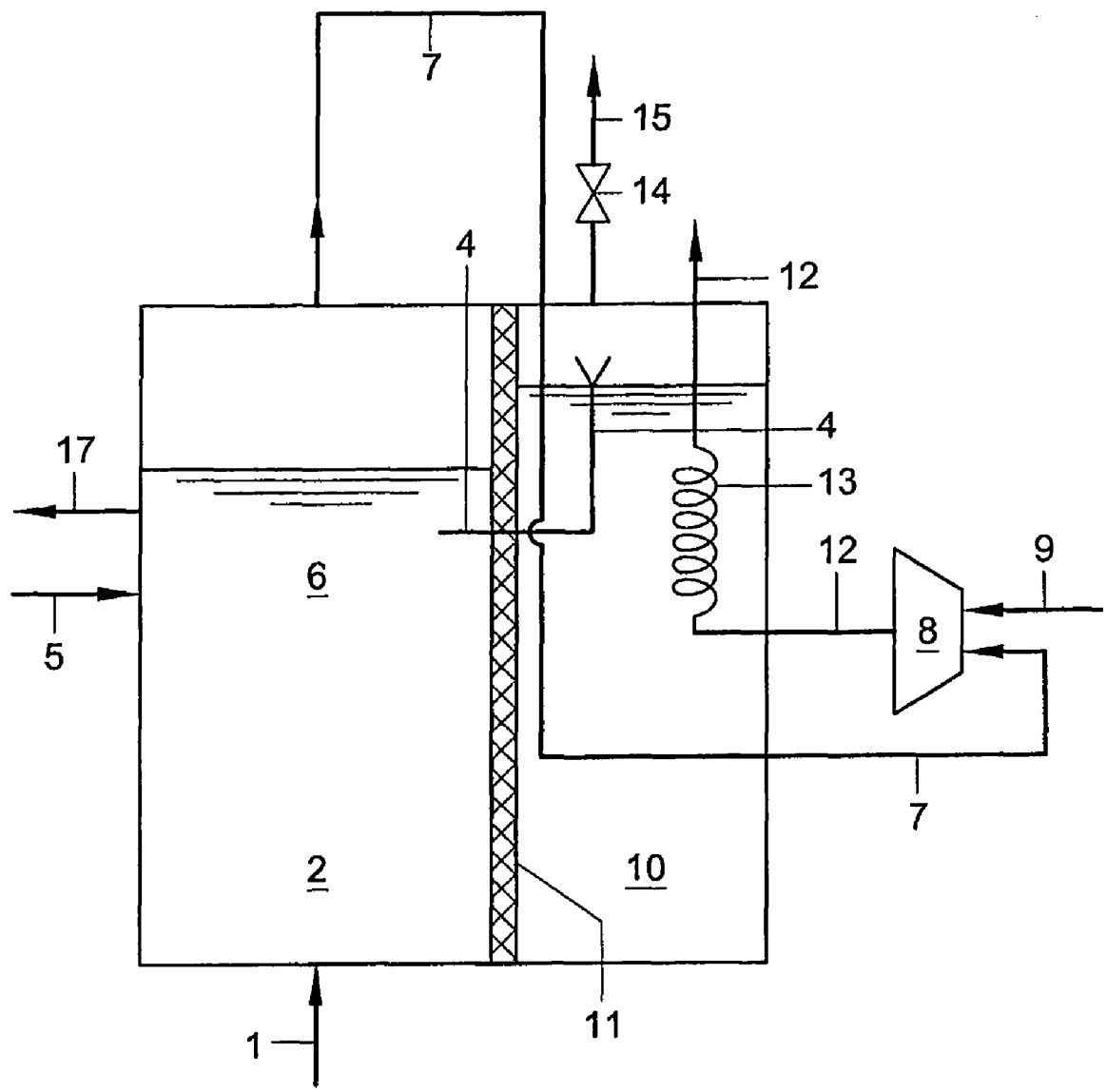

In FIG. 2 a waste water purification unit is shown comprising a housing 2 wherein the first compartment is the anaerobic reactor 6. This means that no separate conditioning compartment is present and the nutrients and heat are introduced directly into the anaerobic reactor. The numbering of the various parts is identical to the numbering in FIG. 1.

It is to be noted that in the FIGS. 1 and 2, the housing 2 is used to house two separate compartments. It is of course equally possible to have separate vessels for the various sections, without deviating from the spirit of the invention.

In the following example waste water is purified in an installation in accordance with FIG. 1.

34 m$^3$/h waste water from a juice-factory plant, containing 3800 mg/l COD having a temperature of 15° C. was introduced in section 3 of the housing 2. The steam, having a temperature of 105° C. (pressure of 1.2 bar (abs) introduced through line 4, at about 2.5 m below the surface heats the water to 25° C. Through line 5 nutrients are introduced and the pH is adjusted to neutral.

The waste water is purified in the reactor 6, resulting in 60 Nm$^3$/h biogas containing 75 vol. % of methane, 25 vol. % $CO_2$ and 100 ppm of $H_2S$.

The biogas was heated in the hot water boiler to a temperature of 105° C. and burned in the burner with air (lambda of 1.15).

Of the steam a part was vented in order to maintain the waste water temperature at 25° C.

The invention claimed is:

1. A process for the anaerobic purification of waste water in an anaerobic reactor, wherein anaerobic sludge is used to purify waste water and to produce biogas, which process comprises
   conditioning waste water in a compartment separate from the said reactor, wherein
   a) said compartment is connected to a hot water boiler by means of a line between the gas head of the boiler and said compartment;
   b) said line connecting the hot water boiler to the compartment ends underneath the waste water level in said compartment at such a level that a pressure of between 0.25 and 3 m of water column is maintained in the gas head of the boiler;
   c) wherein boiler steam generated in the gas head of the boiler enters said compartment through said line and heats the waste water;
   d) biogas generated in the reactor is burned in a gas burner, the hot gases obtained thereby are used for indirect heating of water in the hot water boiler,
   e) said boiler is further provided with a valve to let off steam in case the amount of biogas is in excess of the amount needed to heat the waste water;
   and introducing the waste water, which has been conditioned in a compartment separate from the said reactor in which it is purified, into the reactor; and
   wherein said anaerobic reactor and said boiler are placed adjacent in the same housing, with an insulating wall between them; and/or
   wherein the biogas, as produced, is indirectly heated, prior to the burning thereof, in said boiler; and/or
   wherein the total amount of biogas is fed to said gas burner and exhaust gases of the burner, after indirect heat exchange in said boiler, are vented to the atmosphere; and/or
   wherein said boiler is provided with a second burner, which is suitable for fuel gas or liquid fuel, to be used in case the production of biogas is too low to provide the required heating.

2. A process for the anaerobic purification of waste water in an anaerobic reactor, wherein anaerobic sludge is used to purify waste water and to produce biogas, wherein
   a) said reactor is connected to a hot water boiler by means of a line between the gas head of the boiler and said reactor;
   b) said line connecting the hot water boiler to the reactor ends underneath the waste water level in said reactor at such a level that a pressure of between 0.25 and 3 m of water column is maintained in the gas head of the boiler;
   c) wherein boiler steam generated in the gas head of the boiler enters said reactor through said line and heats the waste water;
   d) biogas generated in the reactor is burned in a gas burner, the hot gases obtained thereby are used for indirect heating of water in the hot water boiler,
   e) said boiler is further provided with a valve to let off steam in case the amount of biogas is in excess of the amount needed to heat the waste water; and
   wherein said anaerobic reactor and said boiler are placed adjacent in the same housing, with an insulating wall between them; and/or
   wherein the biogas, as produced, is indirectly heated, prior to the burning thereof, in said boiler; and/or
   wherein the total amount of biogas is fed to said gas burner and exhaust gases of the burner, after indirect heat exchange in said boiler, are vented to the atmosphere; and/or
   wherein said boiler is provided with a second burner, which is suitable for fuel gas or liquid fuel, to be used in case the production of biogas is too low to provide the required heating.

* * * * *